US012584857B2

(12) United States Patent
Rajavelu Muralidhar et al.

(10) Patent No.: US 12,584,857 B2
(45) Date of Patent: Mar. 24, 2026

(54) METHOD AND APPARATUS FOR TRANSMITTANCE MEASUREMENTS OF LARGE ARTICLES

(71) Applicant: ASM IP Holding B.V., Almere (NL)

(72) Inventors: Shiva K.T. Rajavelu Muralidhar, Tempe, AZ (US); Youness Alvandi-Tabrizi, Tempe, AZ (US); John DiSanto, Scottsdale, AZ (US); Sam Kim, Chandler, AZ (US)

(73) Assignee: ASM IP Holding B.V., Almere (NL)

( * ) Notice: Subject to any disclaimer, the term of this patent is extended or adjusted under 35 U.S.C. 154(b) by 0 days.

(21) Appl. No.: 18/379,312

(22) Filed: Oct. 12, 2023

(65) Prior Publication Data

US 2024/0044792 A1     Feb. 8, 2024

Related U.S. Application Data

(63) Continuation of application No. 17/157,507, filed on Jan. 25, 2021, now Pat. No. 11,828,707.

(60) Provisional application No. 62/970,057, filed on Feb. 4, 2020.

(51) Int. Cl.
| | |
|---|---|
| *G01N 21/59* | (2006.01) |
| *G01B 11/02* | (2006.01) |
| *G01N 21/958* | (2006.01) |
| *G01N 33/207* | (2019.01) |

(52) U.S. Cl.
CPC .......... *G01N 21/59* (2013.01); *G01B 11/028* (2013.01); *G01N 21/958* (2013.01); *G01N 33/207* (2019.01); *G01N 2201/021* (2013.01)

(58) Field of Classification Search
CPC .... G01N 21/59; G01N 21/958; G01N 33/207; G01N 2201/021; G01N 2021/5976; G01N 2291/267; G01B 11/028
See application file for complete search history.

(56) References Cited

U.S. PATENT DOCUMENTS

| | | | |
|---|---|---|---|
| 4,750,133 A | 6/1988 | Eiskamp et al. | |
| 5,216,932 A * | 6/1993 | Takei ..................... | B23Q 1/621 |
| | | | 248/657 |
| 6,042,785 A * | 3/2000 | Harju ................... | G01N 21/255 |
| | | | 356/417 |
| 6,484,608 B1 * | 11/2002 | Ziavras ................... | F24S 30/45 |
| | | | 74/490.09 |

(Continued)

FOREIGN PATENT DOCUMENTS

| | | | | |
|---|---|---|---|---|
| CN | 107064169 A * | 8/2017 | ............. | G01N 21/95 |
| CN | 107976152 A * | 5/2018 | ........... | G01B 5/0002 |

(Continued)

OTHER PUBLICATIONS

English machine translation of CN-107064169-A (Year: 2017).*
English machine translation of CN109342375A (Year: 2019).*
English machine translation of CN107976152A (Year: 2018).*

*Primary Examiner* — Dominic J Bologna
(74) *Attorney, Agent, or Firm* — Snell & Wilmer L.L.P.

(57)     ABSTRACT

Methods and apparatus for measuring light intensity are disclosed. The methods and apparatus can be used to verify an article, such as a reaction chamber. Exemplary apparatus include a first arm, a light source coupled to the first arm, a second arm, and a sensor coupled to the second arm. The sensor can receive light from the light source that is transmitted through at least a portion of the article.

18 Claims, 5 Drawing Sheets

(56)  References Cited

U.S. PATENT DOCUMENTS

| | | | |
|---|---|---|---|
| 11,828,707 B2 * | 11/2023 | Rajavelu Muralidhar | .................. G01N 33/207 |
| 2002/0167660 A1 * | 11/2002 | Zaslavsky | ........ G01N 21/95684 356/237.2 |
| 2012/0120388 A1 * | 5/2012 | Harbers | ................. G01N 21/59 356/73 |
| 2012/0170040 A1 * | 7/2012 | Park | ....................... G01N 21/59 356/432 |
| 2015/0077742 A1 | 3/2015 | Wootton | |
| 2016/0063790 A1 * | 3/2016 | Stewart | ................ G07D 7/1205 356/365 |
| 2017/0088941 A1 * | 3/2017 | Schroeder | .............. G01N 21/55 |
| 2018/0080923 A1 * | 3/2018 | Hall | .................... A61B 10/007 |
| 2021/0181106 A1 * | 6/2021 | Shimizu | ................ G01B 11/24 |

FOREIGN PATENT DOCUMENTS

| | | | | |
|---|---|---|---|---|
| CN | 109342375 A | * | 2/2019 | ............. G01N 21/59 |
| EP | 1371994 A2 | * | 12/2003 | ........... G01B 11/306 |

* cited by examiner

METHOD AND APPARATUS FOR TRANSMITTANCE MEASUREMENTS OF LARGE ARTICLES

CROSS-REFERENCE TO RELATED APPLICATIONS

This application is a continuation of, and claims priority to and the benefit of, U.S. patent application Ser. No. 17/157,507, filed Jan. 25, 2021 and entitled "METHOD AND APPARATUS FOR TRANSMITTANCE MEASURE-MENTS OF LARGE ARTICLES," which is a non-provisional of, and claims priority to and the benefit of, U.S. Provisional Patent Application 62/970,057, filed Feb. 4, 2020 and entitled "METHOD AND APPARATUS FOR TRANSMITTANCE MEASUREMENTS OF LARGE ARTICLES," which are hereby incorporated by reference herein.

FIELD OF INVENTION

The present disclosure relates generally to methods and apparatus for measuring transmittance of light through an object. More particularly, the disclosure relates to methods and apparatus for verifying an object using light intensity and/or transmission measurements.

BACKGROUND OF THE DISCLOSURE

Quartz chambers can be used in a variety of applications. For example, quartz reaction chambers can be used in the manufacture of electronic devices, such as semiconductor devices, photoelectric devices, and the like.

Use of quartz chambers may be desirable for several reasons. For example, quartz material can be relatively inert with respect to precursors and/or reactants used in the manufacture of electronic devices. Further, quartz material exhibits high transparency to light over a wide range or wavelengths, including to light having a wavelength or wavelengths suitable for heating substrates within the quartz chamber during processing.

For several applications, such as vacuum process applications, it may be desirable to reinforce the quartz chamber using, for example, ribs of quartz material that can be welded to a surface of the quartz chamber. Such features (e.g., welds and/or ribs) may exhibit a different transparency to light of certain wavelengths, compared to a wall of the quartz chamber, particularly at an interface of the feature and the chamber wall. Further transparency of the features and/or the wall can vary across the reaction chamber. Such variation can result in a variation in an amount of heat or radiation supplied to a substrate.

Because of their relatively large size, it can be difficult to measure an intensity of light (or a transmittance of light) at multiple points of the reaction chamber wall and of the features, let alone to accurately measure the intensity and/or transmittance. Accordingly, improved methods and apparatus for measuring light intensity of transmittance of light through objects, particularly of large objects, are desired.

Any discussion, including discussion of problems and solutions, set forth in this section, has been included in this disclosure solely for the purpose of providing a context for the present disclosure, and should not be taken as an admission that any or all of the discussion was known at the time the invention was made or otherwise constitutes prior art.

SUMMARY OF THE DISCLOSURE

This summary is provided to introduce a selection of concepts in a simplified form. This summary is not intended to necessarily identify key features or essential features of the claimed subject matter, nor is it intended to be used to limit the scope of the claimed subject matter.

In some embodiments, methods of verifying an article having features thereon are provided. Exemplary methods include providing an apparatus, using the apparatus to measure a transmittance of light from the light source through a wall of the article, and determining a quality of the article based on measured transmittance values. The apparatus can include a first arm, a light source coupled to the first arm, a second arm, and a sensor coupled to the second arm. The article can be or include, for example, a reaction chamber. The methods can be used to determine a quality and/or a dimension (e.g., a width) of a feature, such as a feature (e.g., rib that is welded to a wall of the reaction chamber and/or a width of the weld). The light source can be outside or inside the reaction chamber. Similarly, the sensor can be inside or outside the chamber. The first and second arms can be moved together to measure multiple transmittance values—e.g., along a path (e.g., a line) of movement of the two arms. Other methods are also described below.

In accordance with additional embodiments of the disclosure, apparatus for verifying an article are provided. Exemplary apparatus can include a first arm, a light source coupled to the first arm, a second arm, and a sensor coupled to the second arm. The light source can emit light through the article and the sensor can receive light that is transmitted through the article. The article can include, for example, a (e.g., quartz) reaction chamber. The apparatus can further include a reflective surface coupled to the first or the second arm to direct light in a desired direction (e.g., from the light source toward the sensor). Exemplary apparatus can include a shield—e.g., coupled to the first or second arm. The apparatus can further comprise a member coupled to the first arm and the second arm. The apparatus can also include one or more motors to cause the first arm and the second arm to move in one or more (e.g., two) directions. Exemplary apparatus can include one or more data acquisition devices to receive information from the sensor. The apparatus can further include a database that stores information, such as measured intensity and/or transmittance values, coordinates associated with the measurements, and an identity associated with one or more articles. Other apparatus are also disclosed.

In accordance with further examples of the disclosure, a system can include an apparatus as described herein. The system may further include an article to be measured and/or a fixture for retaining the article.

These and other embodiments will become readily apparent to those skilled in the art from the following detailed description of certain embodiments having reference to the attached figures, the invention not being limited to any particular embodiment(s) disclosed.

BRIEF DESCRIPTION OF THE DRAWING FIGURES

While the specification concludes with claims particularly pointing out and distinctly claiming what are regarded as embodiments of the invention, the advantages of embodiments of the disclosure may be more readily ascertained from the description of certain examples of the embodiments of the disclosure when read in conjunction with the accompanying drawings.

It will be appreciated that elements in the figures are illustrated for simplicity and clarity and have not necessarily been drawn to scale. For example, the dimensions of some of the elements in the figures may be exaggerated relative to other elements to help improve understanding of illustrated embodiments of the present disclosure.

DETAILED DESCRIPTION OF EXEMPLARY EMBODIMENTS

Although certain embodiments and examples are disclosed below, it will be understood by those in the art that the invention extends beyond the specifically disclosed embodiments and/or uses of the invention and obvious modifications and equivalents thereof. Thus, it is intended that the scope of the invention disclosed should not be limited by the particular disclosed embodiments described below.

The illustrations presented herein are not necessarily meant to be actual views of any particular apparatus or data, but may merely be idealized representations that are used to describe embodiments of the disclosure.

Figure 1:
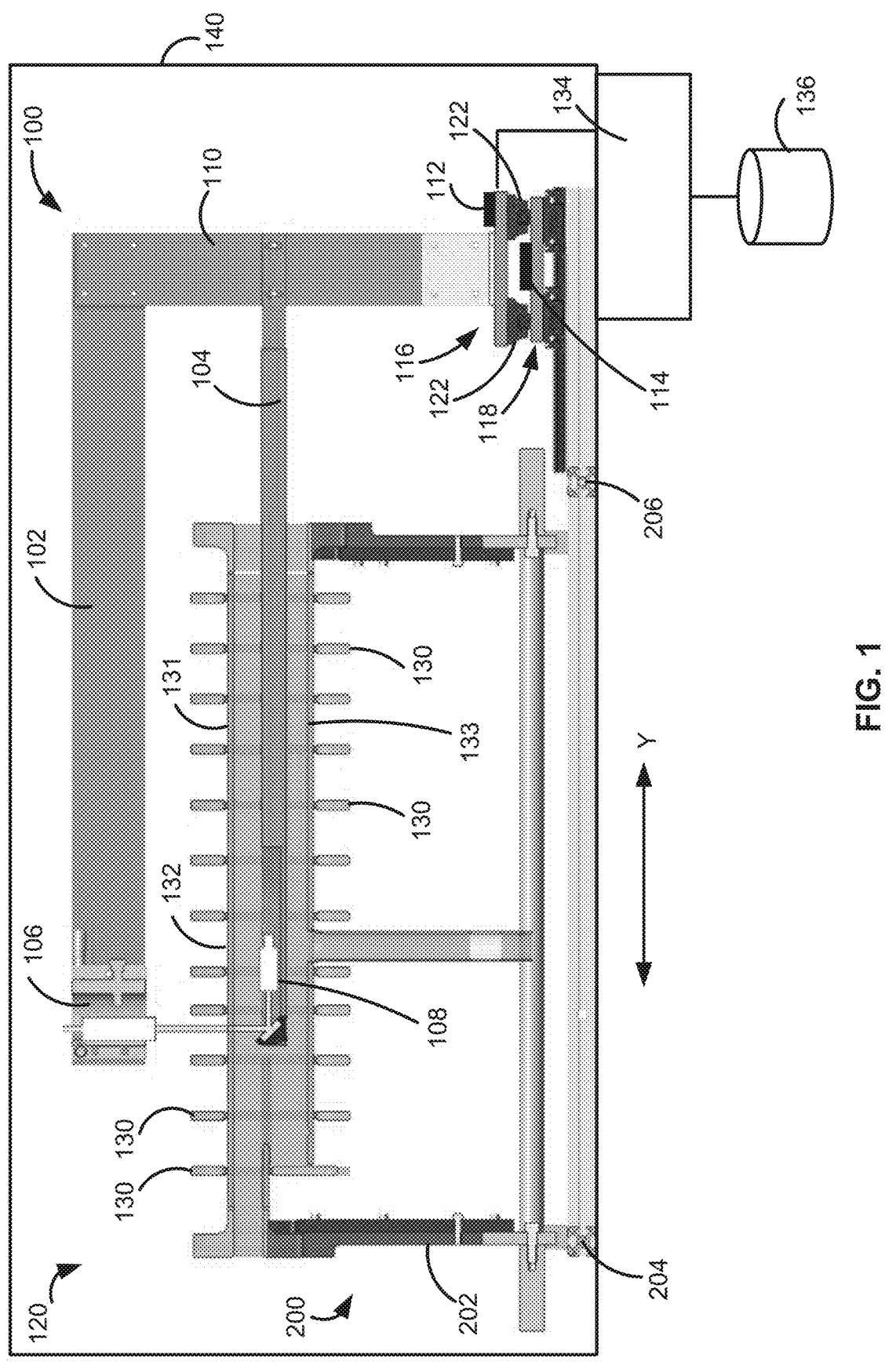
FIG. 1 illustrates a side view of an apparatus in accordance with examples of the disclosure.
Figure 2:
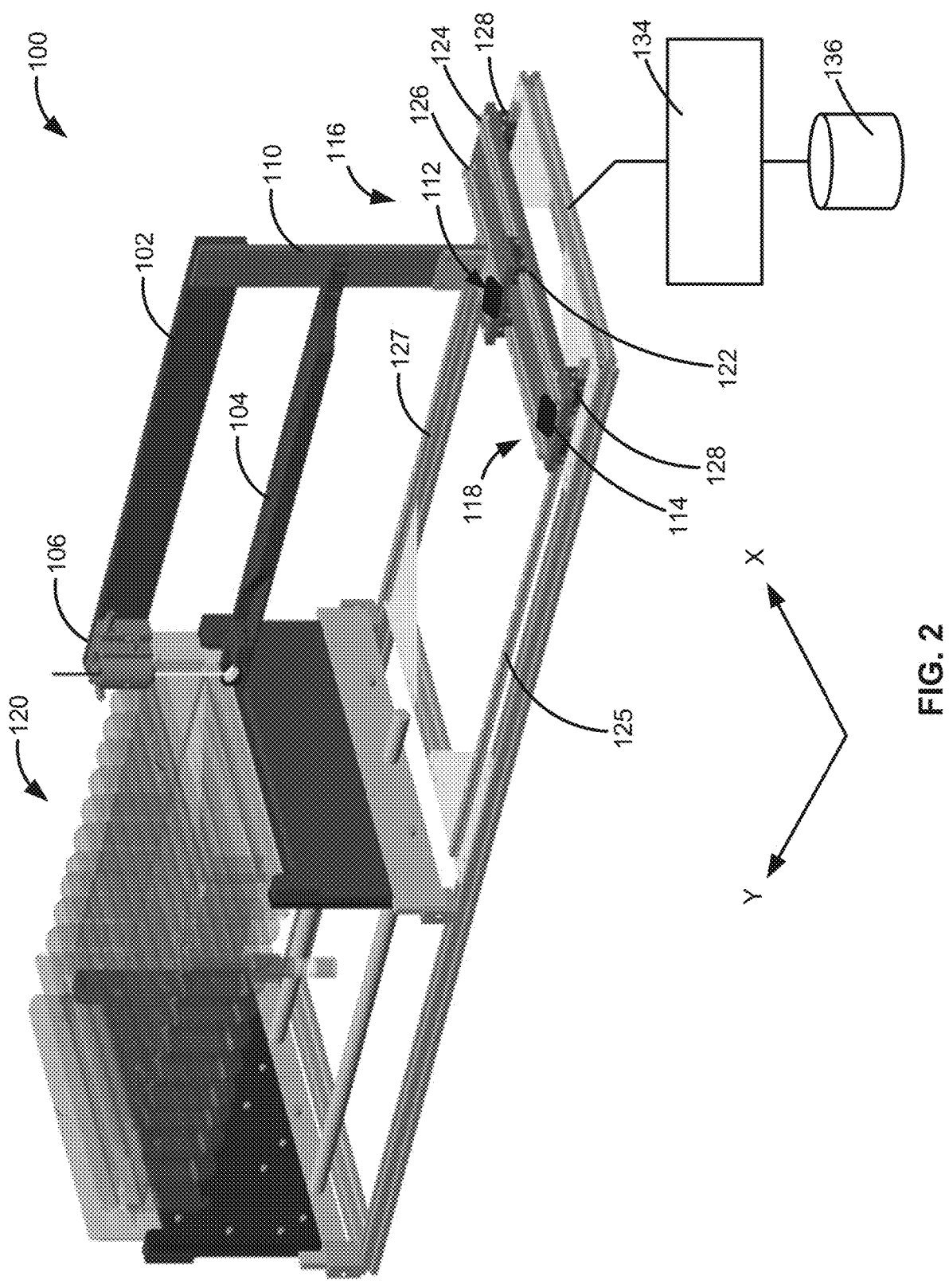
FIG. 2 illustrates a perspective view of the apparatus illustrated in FIG. 1.
Figure 3:
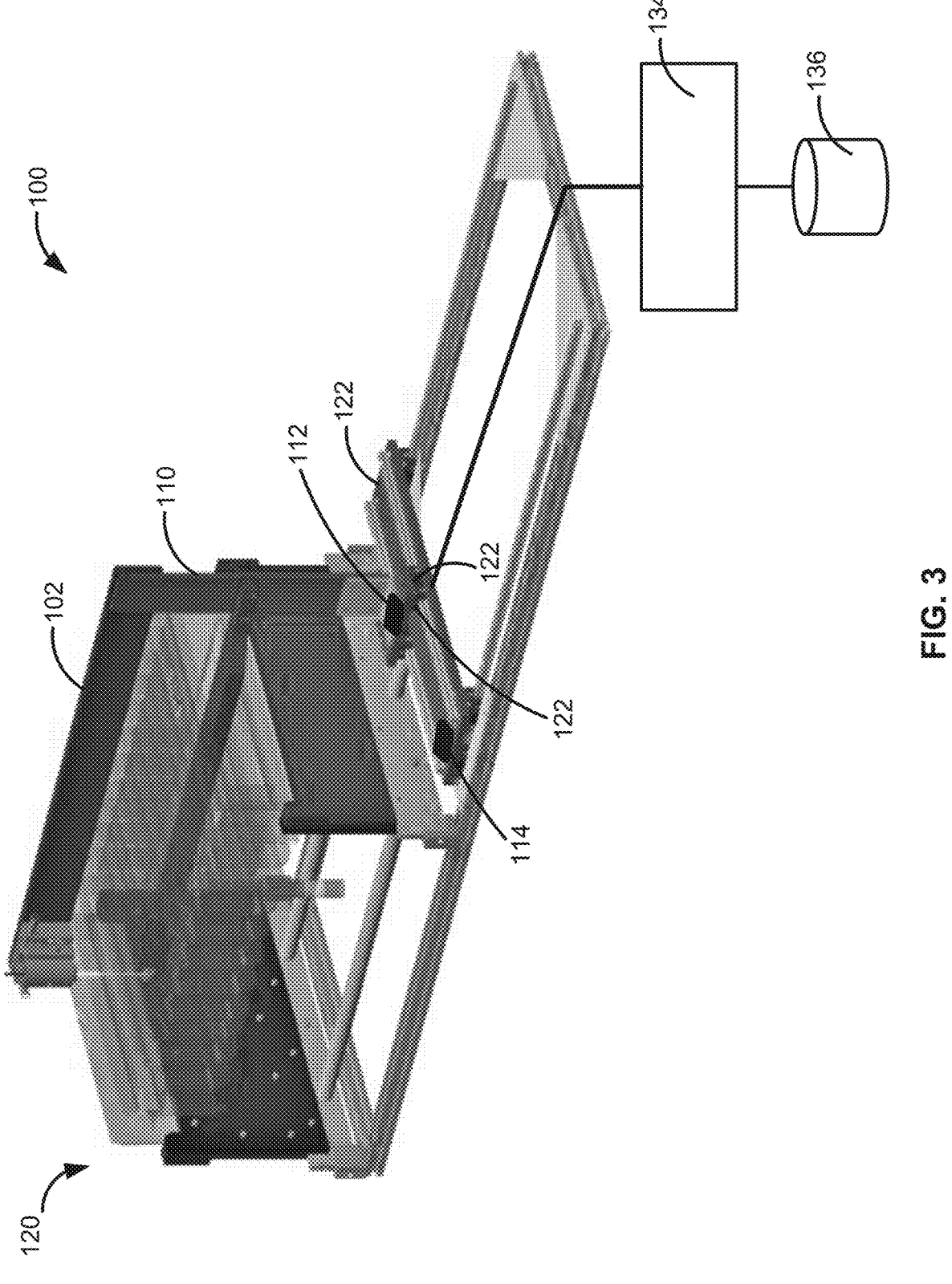
FIG. 3 illustrates another perspective view of the apparatus illustrated in FIG. 1.
Figure 4:
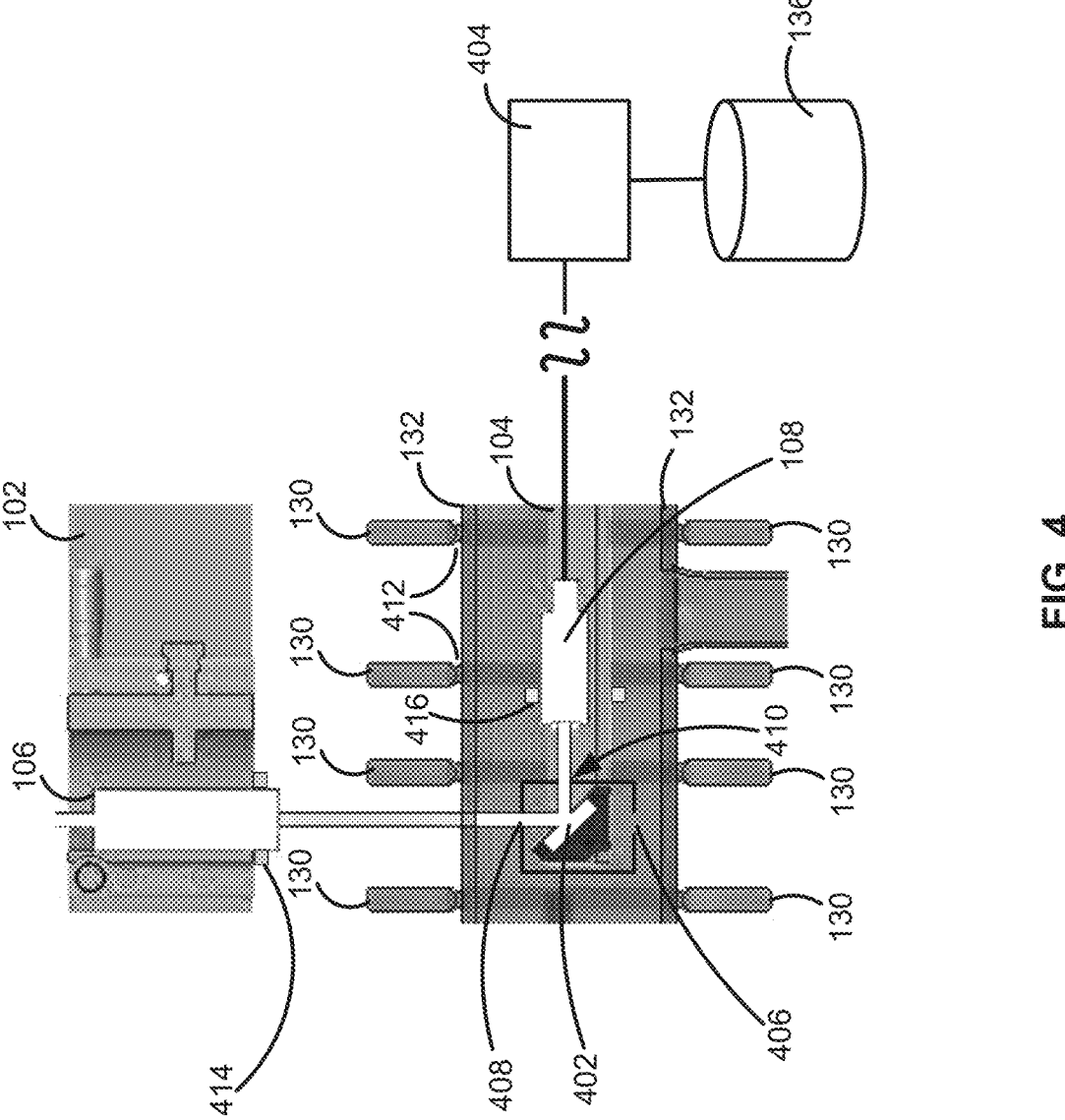
FIG. 4 illustrates an enlarged view of a light source and a sensor in accordance with examples of the disclosure.

Turning now to the drawing figures, FIG. 1 illustrates an apparatus 100 in accordance with exemplary embodiments of the disclosure. Apparatus 100 includes a first arm 102, a second arm 104, a light source 106 coupled to first arm 102, and a sensor 108 coupled to second arm 104. Apparatus 100 also includes a member 110, a first motor 112, a second motor 114, a first movement device 116, and a second movement device 118. FIG. 1 illustrates a side view of apparatus 100 with second arm 104 partially inserted into reaction chamber 120; FIG. 2 illustrates apparatus 100, with second arm 104 exterior to reaction chamber 120; FIG. 3 illustrates apparatus 100, with second arm 104 inserted within reaction chamber 120; FIG. 4 illustrates a close-up view of ends of first arm 102, second arm 104, light source 106, and sensor 108.

Various examples of the present disclosure provide methods and apparatus for measuring intensity of light transmitted through an article. The measured light intensity can be used to calculate a transmittance of the light through the article using the formula: transmittance=sample beam intensity/reference beam intensity. In other words, transmittance of light through the article can be calculated by comparing measured light intensity to a reference beam intensity. The reference beam intensity can be the intensity measured between light source 106 and sensor 108 when an article is not interposed between light source 106 and sensor 108—e.g., when nothing is between light source 106 and sensor 108. As set forth in more detail below, measured transmittance values can be used to verify an article (e.g., a go or no go for the article) based on, for example, comparison of measurements to values of known good articles and/or known bad articles.

During operation, a method of measuring light intensity, measuring transmittance, and/or of verifying an article can include providing an article, such as a reaction chamber 120, providing one of the first arm 102 and the second arm 104 on one side (e.g., within) of the article and the other of the first arm 102 and the second arm 104 on another side (e.g., outside) of the article to thereby measure one or more of light intensity and transmittance through the article or through a wall of the article. In the illustrated example, second arm 104 extends into reaction chamber 120 and first arm 102 is exterior to reaction chamber 120. In this case, light intensity and/or transmittance is measured through an upper section 131 of a wall 132 of reaction chamber 120. In accordance with other examples, first arm 102 can be placed within reaction chamber 120 and second arm 104 can be exterior to reaction chamber 120 to measure a lower section 133 of wall 132. In accordance with some examples, one or more (e.g., an array of) sensors 108 can be coupled to second arm 104 within an article (e.g., reaction chamber) an be and/or traverse along a plane that would include a substrate during processing. This allows measuring actual irradiance of IR on the substrate and characterize the irradiation variation from tool to tool. Such techniques can assist with calibrating the articles/reaction chambers.

First arm 102 can comprise any suitable material. For example, first arm 102 can be formed of thermoplastic, such as Ultem. A length of first arm 102 can be such that to measure reaction chamber 120 or other articles ranging from, for example, about 1 mm to about 1000 mm, or higher.

Similarly, second arm 104 can comprise any suitable material—e.g., a thermoplastic, such as Ultem. Member 110 can also be formed of any suitable material, such as a metal Apparatus 100 can be used to measure large articles, such as reaction chamber 120. In accordance with examples, of the disclosure, an article can be about 1 mm to about 1000 mm in length and/or about 1 to about 750 mm in width.

First arm 102 can be fixedly or removably attached to member 110. By way of examples, first arm 102 can be welded, adhered to (e.g., using an adhesive, such as glue), and/or attached using one or more couplers, such as bolts, screws, rivets, or the like. Similarly, second arm 104 can be fixedly or removably attached to member 110 using the same or similar techniques.

A length of first arm 102 and/or a length of second arm 104 can be adjustable to allow for measuring articles of various lengths. Similarly, a length of member 110 can be adjustable and/or a distance between first arm 102 and second arm 104 can be adjustable.

In the illustrated example, member 110 is attached to a first movement device 116. First movement device 116 can include a first motor 112 and rotatable objects (e.g., wheels) 122 coupled to first motor 112. First motor 112 can be mechanically coupled to rotatable objects 122 to cause member 110 and hence first arm 102 and second arm 104 to move in a first (e.g., X) direction—e.g., along rails 124, 126. Member 110 can be fixedly or removably attached to movement device 116—e.g., using techniques described above.

Second movement device 118 includes a second motor 114 and rotatable objects (e.g., wheels) 128. Second motor 114 can be mechanically coupled to rotatable objects 128 to cause member 110 and hence first arm 102 and second arm 104 to move in a second (e.g., Y) direction—e.g., along rails 125, 127. Rails 124-127 can be formed of any suitable material, such as metal—e.g., aluminum.

Additionally or alternatively, first and second arms 102, 104 can extend in or out in the Y direction (away from or toward member 110) using, for example, a screw motor, while member 110 does or does not move the same distance. Further, first and second movement devices 116, 118 may additionally or alternatively include other devices, such as linear screw mechanisms or the like.

Light source 106 can include a light source that emits light that includes light that is at least partially transmitted by at least a portion of an article, such as reaction chamber 120. By way of examples, light source 106 can include a source that emits light having one or more wavelengths in the range of ultraviolet to infrared electromagnetic waves. In some cases, light source 106 can emit visible light. In some cases, light source 106 can emit infrared radiation. In some cases, light source 106 can emit ultraviolet radiation. In accordance with some examples, light emitted from light source 106 can have a single wavelength or multiple wavelengths in the range of ultraviolet to infrared electromagnetic waves. Light source 106 can be selected to emit the same, similar (e.g., within about +/– ten percent), or a subset of wavelength(s) of light emitted by one or more heaters used to heat a substrate within reaction chamber 120. In some cases, light source 106 includes one or more lasers. Light source 106 can also include one or more lenses and/or apertures to focus and/or columnate the emitted light. Although illustrated with one light source 106, apparatus in accordance with this disclosure can include one or more light sources 106 coupled to first arm 102. An alignment device 414 can be used to facilitate alignment of light source 106 with sensor 108. Further, light source 106 can be tilted at desired angles using alignment device 414 or another device.

In accordance with other examples of the disclosure, light source 106 can include one or more lamps (e.g., infrared lamps), which can be coupled to first arm 102 or to another fixture. In these cases, sensor 108 can be used to measure light intensity from the one or more lamps at various locations within reaction chamber 120. When the one or more light sources include a plurality of light sources, interaction of light emitted from the one or more light sources and/or shadow effects (e.g., from one or more structures) can be measured. In these cases, the apparatus can be used to determine variation associated with the one or more lamps—e.g., a distance between the lamps and the reaction chamber, an output of the lamps, an orientation of the lamps, or the like.

Sensor 108 includes a device to detect intensity of light transmitted through a portion of an article—e.g., a wall of reaction chamber 120. Sensor 108 can include, for example, a photodiode, a thermopile, or the like. Sensor 108 can be aligned on second arm 104 to receive light from light source 106—for example, a center point of light emitted from light source 106 can be aligned with a center point of sensor 108. In some cases, sensor 108 can include a filter, such that sensor 108 is configured to measure intensity of one or more predetermined wavelengths and/or to filter out one or more wavelengths of light that are not to be measured. Although illustrated with one sensor 108, apparatus in accordance with this disclosure can include one or more sensors 108 coupled to second arm 104.

In some cases, sensor 108 can be aligned within the light path of light source 106 to directly receive light from light source 106. In other cases, a reflective surface (e.g., a mirror) 402 can be used to direct light from light source 106 to sensor 108. An alignment device 416 can be used to facilitate alignment of sensor 108 with light source 106 and/or mirror 402. Further, sensor 108 can be tilted at desired angles using alignment device 416 or another device.

In addition, as illustrated in FIG. 4, apparatus 100 can include a shield 406 to mitigate scattering of light. Shield 406 can be formed of, for example, plastic or ceramic material to mitigate any metal contamination within reaction chamber 120. Shield 406 can include a first aperture 408. First aperture 408 can be smaller than a diameter of a beam of light from light source 206—e.g., to columnate the beam of light. Additionally or alternatively, shield 406 can include an aperture 410 between light source 106 or mirror 402 and sensor 108.

Reaction chamber 120 or other articles can be formed of, for example, quartz, or other material that is at least partially transparent to wavelength of the light emitted from light source 106. As illustrated in the figures, reaction chamber 120 can include support structures 130 (e.g., ribs) that provide support to reaction chamber 120 when, for example, a pressure within reaction chamber 120 is different (e.g., lower) than a pressure exterior to reaction chamber 120. Support structures 130 can be integrally formed on a wall 132 of reaction chamber 120. Alternatively, support structures 130 can be welded or otherwise attached to wall 132.

For measurement, reaction chamber 120 can be coupled to a fixture 200, which includes a frame 202. Frame 202 can be formed of any suitable material, such as, for example, plastic.

Fixture 200 and/or apparatus 100 can include vibration dampening devices 204, 206 to mitigate any vibration from the surrounding environment and/or that may arise during use of apparatus 100. In some cases, vibration dampening devices can include resilient material.

Apparatus 100 can also include a controller 134 to cause first movement device 116 and/or second movement device 118 to move to desired locations. In accordance with examples of the disclosure, controller 134 can include a processor and memory to cause first movement device 116 to move to a desired location and then cause second movement device 118 to move to a plurality of locations in the Y direction to obtain intensity and/or transmittance measurements in the Y direction as illustrated in, for example, FIGS. 1-3. In accordance with examples of the disclosure, controller 134 can cause first movement device 116 to move in increments. Additionally or alternatively, controller 134 can cause second movement device 118 to move in increments. Additionally or alternatively, controller 134 can cause first arm 102 and second arm 104 to extend and retract in the Y direction.

Apparatus 100 can also include a data acquisition device 404, illustrated in FIG. 4. Data acquisition device 404 can include a processor and memory to collect and store intensity and/or transmittance values received from sensor 108. In some cases, data acquisition device 404 can form part of controller 134. In other cases, data acquisition device 404 can be a standalone device.

Apparatus 100 can also include a database 136 to store intensity and/or transmittance values, which can be associated with a location of an article, such as reaction chamber 120. By way of examples, database 136 can include article identification information, transmittance information and location information (e.g., X and Y coordinates) for multiple intensity/transmittance measurements, known good values for intensity/transmittance measurements, and/or known bad values for intensity/transmittance measurements. Database 136 can be a standalone device, or can form part of another device, such as controller 134, or the like.

Controller 134 can be configured to cause apparatus 100 to measure one or more intensity/transmittance measurements at one site, such that database 136 receives one or more values associated with each site. In the case of multiple measurements per site, data acquisition device 404 and/or another device can average the values for each site, and the values, average values, and/or a deviation (e.g., a standard deviation) of the measured values for each site and/or average values for each site and for each article can be stored.

As illustrated in FIG. 1, apparatus 100 can also include a housing 140. Housing 140 can encase apparatus 100 and can mitigate any light from light source 106 escaping to a surrounding environment and/or can mitigate environmental effects on the measured values.

Figure 5:
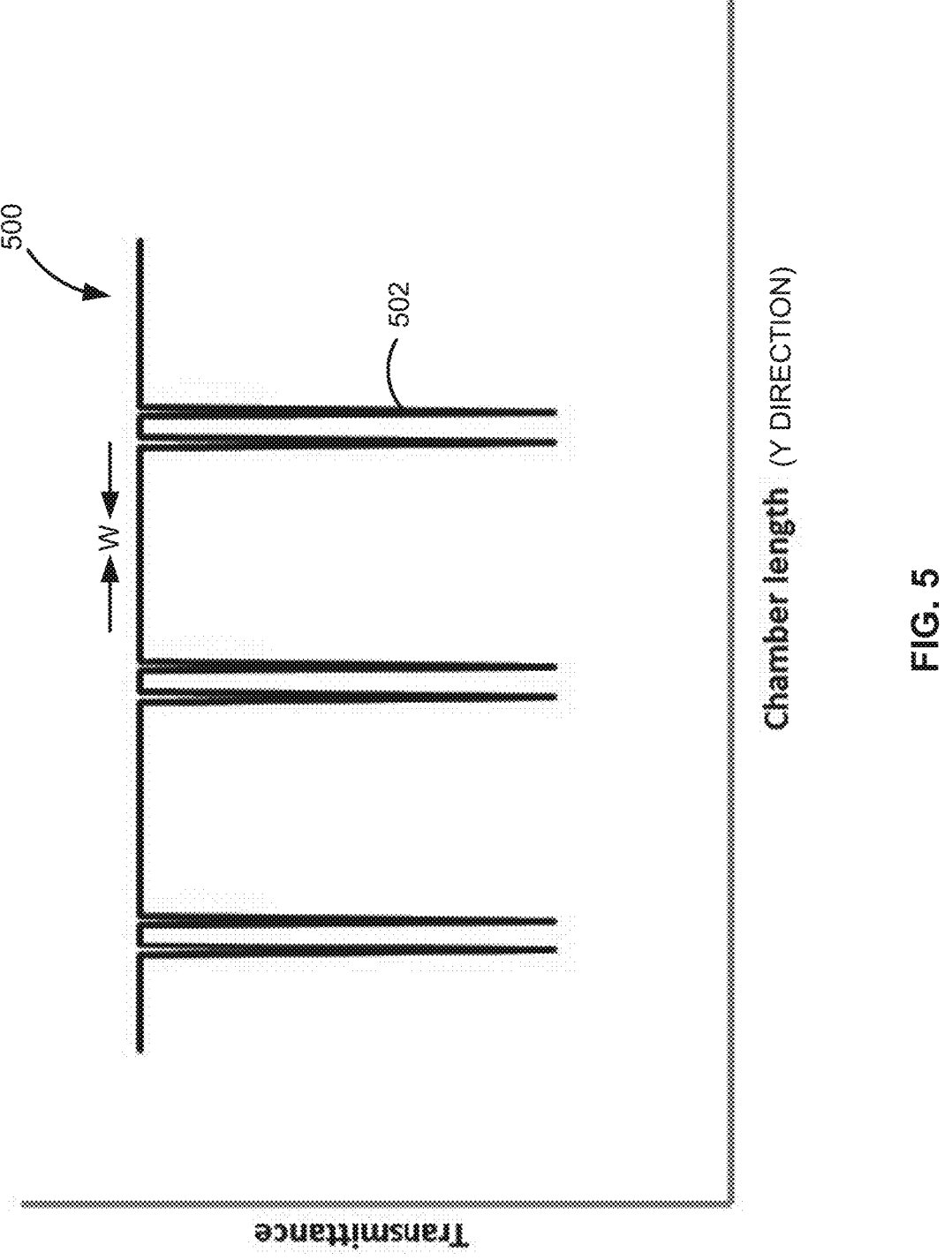
FIG. 5 illustrates transmittance values measured in accordance with examples of the disclosure.

FIG. 5 illustrates transmittance measurements 500 taken along a Y direction of reaction chamber 120. As illustrated, transmittance measurements 500 include perturbations 502, which can correspond to support structures or features 130 (e.g., an edge of a structure/feature) and/or welds 412 coupling support structures 130 to wall 132. A width, W, of one or more perturbations 502 can be analyzed to determine whether a weld 412 (e.g., a width of the weld) or other feature is within acceptable tolerances—e.g., by comparing measured intensity and/or transmittance values to known good or known bad values. Additionally or alternatively, other intensity or transmission measurements can be compared to values of known good articles (e.g., reaction chambers) to verify whether transmission of wavelength(s) of light is within an acceptable range.

The example embodiments of the disclosure described above do not limit the scope of the invention, since these embodiments are merely examples of the embodiments of the invention, which is defined by the appended claims and their legal equivalents. Any equivalent embodiments are intended to be within the scope of this invention. Indeed, various modifications of the disclosure, in addition to those shown and described herein, such as alternative useful combination of the elements described, may become apparent to those skilled in the art from the description. Such modifications and embodiments are also intended to fall within the scope of the appended claims.

What is claimed is:

1. An apparatus for verifying an article, the apparatus comprising:
   a first arm;
   a light source coupled to the first arm;
   a second arm;
   a first motor to cause the first arm and the second arm to move in a first direction;
   a second motor to cause the first arm and the second arm to move in a second direction;
   a member coupled to the first arm and the second arm, wherein a distance between the first arm and the second arm is adjustable;
   a reflective surface coupled to the second arm;

a sensor coupled to the second arm, wherein the sensor is configured to measure light intensity; and
   a shield coupled to the second arm, wherein the shield comprises a first aperture disposed between the light source and the reflective surface and a second aperture disposed between the reflective surface and the sensor,
   wherein the light source emits light through the article,
   wherein the first direction and the second direction are linear directions, and
   wherein the sensor receives light from the light source that is transmitted through the article.

2. The apparatus of claim 1, wherein the first direction and the second direction are horizontal directions.

3. The apparatus of claim 1, wherein the first and second arms are configured to move in the first direction for a distance while the member does not move the same distance.

4. The apparatus of claim 1, wherein the first arm and the second arm are extendible in the first direction.

5. The apparatus of claim 1, further comprising a data acquisition device to receive information from the sensor.

6. The apparatus of claim 5, further comprising a database coupled to the data acquisition device.

7. The apparatus of claim 1, wherein the shield comprises plastic or ceramic material.

8. The apparatus of claim 7, wherein at least some of the light from the light source is directed through the first aperture, and wherein the diameter of a light beam from the light source is greater than the diameter of the first aperture.

9. The apparatus of claim 1, wherein the light source emits light having a wavelength in the range of ultraviolet to infrared electromagnetic waves.

10. The apparatus of claim 1, wherein the reflective surface is configured to direct light from the light source to the sensor.

11. The apparatus of claim 1, wherein the light source comprises an infrared lamp.

12. The apparatus of claim 1, wherein the light source comprises a laser.

13. The apparatus of claim 1, wherein the first arm comprises a thermoplastic.

14. The apparatus of claim 1, wherein the first arm is removably attached to the member.

15. The apparatus of claim 14, wherein the second arm is removably attached to the member.

16. The apparatus of claim 1, wherein the first arm is coupled to the member at a point on the member different from a point where the second is coupled to the member.

17. The apparatus of claim 1, wherein the member is removably attached to a first movement device.

18. A system for verifying a reaction chamber, the system comprising an apparatus according to claim 1.

* * * * *